United States Patent
Wong

(10) Patent No.: US 6,702,577 B2
(45) Date of Patent: Mar. 9, 2004

(54) DENTAL OR SURGICAL ILLUMINATED MIRROR

(75) Inventor: Chan Wong, Hong Kong (CN)

(73) Assignee: Carl Parker Associates, Inc., Hauppauge, NY (US)

( * ) Notice: Subject to any disclaimer, the term of this patent is extended or adjusted under 35 U.S.C. 154(b) by 0 days.

(21) Appl. No.: 10/137,916

(22) Filed: May 1, 2002

(65) Prior Publication Data

US 2003/0207229 A1 Nov. 6, 2003

(51) Int. Cl.[7] .................................................. A61C 3/00
(52) U.S. Cl. ........................................................ 433/30
(58) Field of Search ............................... 433/29, 30, 31; 600/246, 247, 248; 359/882

(56) References Cited

U.S. PATENT DOCUMENTS

| | | | | |
|---|---|---|---|---|
| 938,525 A | * | 11/1909 | Turney | |
| 1,201,550 A | * | 10/1916 | Brush | |
| 1,220,252 A | * | 3/1917 | Matthews | |
| 2,107,791 A | * | 2/1938 | Henning | |
| 2,130,388 A | * | 9/1938 | Gluck | |
| 2,296,793 A | * | 9/1942 | Kirschbaum | |
| 3,032,879 A | * | 5/1962 | Lafitte | |
| 4,080,476 A | * | 3/1978 | Laskey | |
| 4,212,105 A | * | 7/1980 | Hukuba | 433/30 |
| 2002/0058230 A1 | * | 5/2002 | Savin et al. | 433/31 |

* cited by examiner

Primary Examiner—Cary E. O'Connor
(74) Attorney, Agent, or Firm—Alfred M. Walker

(57) ABSTRACT

An ergonomic non-obstructive illuminated examination mirror for dentistry, medicine and surgery, without the need of fiber optics, includes a slim line elongated member having a wire connection passage, a weighted first proximal end with a battery chamber and a second distal end. A removable disposable non-fogging angled reflective mirror head is coupled to the second end of the elongated member. Light to the mirror is provided by a low heat emitting light source attached to the second end of the rod directed toward the angled reflective head. The power source is connected to the low heat light source by one or more conductive wires within the wire passage and a switch, thereby forming a circuit with the power source and the light source, which is activated by a switch connected to the conductive wire connection.

17 Claims, 2 Drawing Sheets

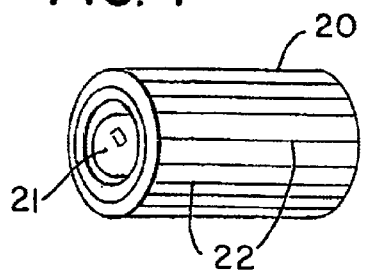
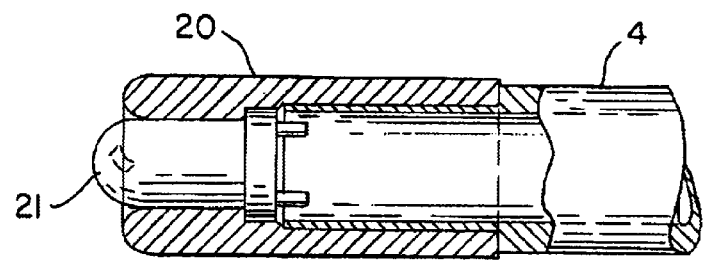
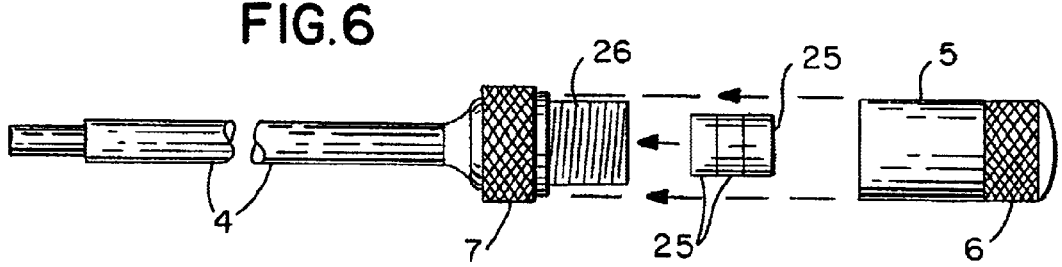
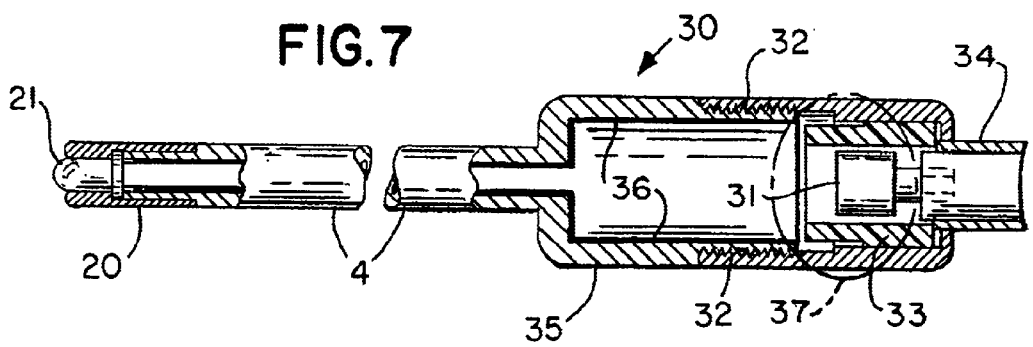

DENTAL OR SURGICAL ILLUMINATED MIRROR

FIELD OF THE INVENTION

The present invention relates to ergonomic illuminated dental or surgical mirrors.

BACKGROUND OF THE INVENTION

Small mirrors with extended handled have been in common use for aiding dental or oral surgical procedures. In addition, it has been found beneficial to combine such an instrument with a light source that impinges light directly on the reflective mirror surface.

Meitzler (U.S. Pat. No. 1,817,417) describes a mirror instrument with a small incandescent lamp at the distal end of the handle portion. A shield is used to minimize the chance of patient tissue contact with the hot lamp surface. A cable is used to supply power to the lamp from a stationary source.

Verderber (U.S. Pat. No. 5,139,421) has a mirror light with two embodiments. In one version, it is a self-contained instrument with battery power source and lamp in the handle portion. Light is conveyed to the distal end adjacent the mirror head through a light pipe so as to eliminate the exposure of the patient to the hot incandescent lamp. In an alternate embodiment, light from a stationary lamp and power source is conveyed using a fiber optic cable to the handpiece of the instrument.

A problem with existing dental examination mirrors is that they need to be held tightly by their whole weight within the tips of the user's thumb and fore finger. This manual manner of holding a dental examination mirror tends to induce jerky, stress inducing movements of the fingers tightly holding the mirror. Besides stress on the finger's of the user, any spasmodic movements of the mirror in this position of holding reduces its efficiency to clearly visualize the object sought to be viewed within the mouth the patient.

SUMMARY AND OBJECTS OF THE INVENTION

It is therefore an object of the invention to provide an ergonomic lighted mirror instrument of light weight and beneficial weight distribution.

It is a further object to provide a self-contained instrument with a long battery life.

It is also an object of the invention to eliminate any exposure of the patient to heat from a light source.

It is a further object to provide white light illuminating surfaces with truer color rendering.

It is also an object of this invention to use disposable mirror refills which simply slip on to the distal end of the instrument to enhance hygiene.

SUMMARY OF THE INVENTION

To achieve these objectives and others which may become apparent, a cool lamp such as a white light-emitting diode (LED) is preferably used for illumination. Due to the very high efficiency of this type of device, its surface remains cool and presents no burning hazard. Also, long battery life from small button cells is possible.

The dental mirror is lit by the small LED lamp at the distal end of a shank handle. Both the mirror and its collar are removable and disposable after each use.

The lamp directs light onto the mirror. The lamp is powered by a battery in the proximal handle end, which is activated by a rotating threaded switch. The lamp is connected by wires within the shank. The reflective surface of the mirror has anti-fogging capabilities.

By using this type of power source instead of tubular cells, they can be housed in a short larger diameter tube at the proximal end of the instrument whereby the weight is concentrated in the webbed edge of the palm of the user's hand between the thumb and fore finger. This enables the mirror to positioned at a distal end of a thin shank, which reduces visual and physical obstruction during use, then extends to the distal end supporting the mirror head.

Preferably, the weight of the short, larger diameter tube housing the batteries contains most of the weight of the unit. For example, in a typical mirror, the weight of the short, heavier battery accommodating distal end portion is about 1.3 ounces in weight, compared to an overall weight of the entire mirror itself is about 1.5 ounces. In that preferable example, the shorter, heavier battery accommodating distal end portion contains about 87 percent of the total weight of the dental mirror.

Moreover, the slender lightweight elongated shank handle is less than ¼ inch in diameter, to minimize visual obstruction of the user's view to the lighted mirror.

Therefore, the fulcrum is concentrated at the proximal battery accommodating end of the dental mirror, which allows for the thin, lightweight shank handle having the mirror and light to extend outward toward the distal end thereof. Therefore, a user can support the heavier weighted proximal end in the webbed edge of the palm between the thumb and fore finger, while gently manipulating between the tips of the thumb and fore finger the shank handle holding the mirror and light at its distal end.

This manner of holding the dental mirror permits subtle manual movements of the mirror during oral examinations, instead of jerky stress inducing movements caused by the necessity of holding the whole weight of prior art mirror tightly between the thumb and fore finger. These ergonomic features enhance the usability of the invention and reduce fatigue during long procedures.

BRIEF DESCRIPTION OF THE DRAWINGS

The present invention can best be understood in connection with the accompanying drawings. It is noted that the invention is not limited to the precise embodiments shown in drawings, in which:

FIG. 4 is a Perspective view of an LED housing used with the illuminated mirror instrument;

FIG. 5 is a Side crossectional view of the LED thereof in a housing;

FIG. 6 is an Exploded side elevational view of the illuminated mirror instrument, shown with the mirror head removed; and, FIG. 7 is a Side crossectional view of an alternate embodiment for an illuminated mirror instrument, using a push-button switch.

DETAILED DESCRIPTION OF THE INVENTION

Figure 1:
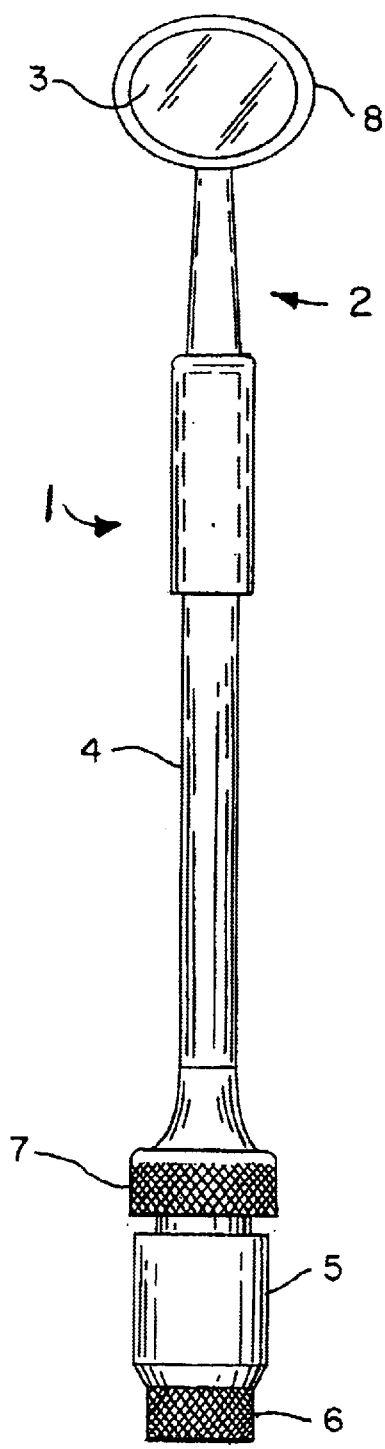
FIG. 1 is a Top plan view of an illuminated mirror instrument of this invention.

A preferred embodiment for an illuminated mirror 1 is shown in FIG. 1. Slender elongated shank member 4, such as a tubular shank, connects battery housing chamber 5 at the proximal end to disposable mirror refill 2 at the distal end. Knurled collar 7 attached to elongated shank member 4 is an aid in disassembly for battery replacement. Knurled ring 6 operates a switch, such as a rotary on/off power switch.

Figure 2:
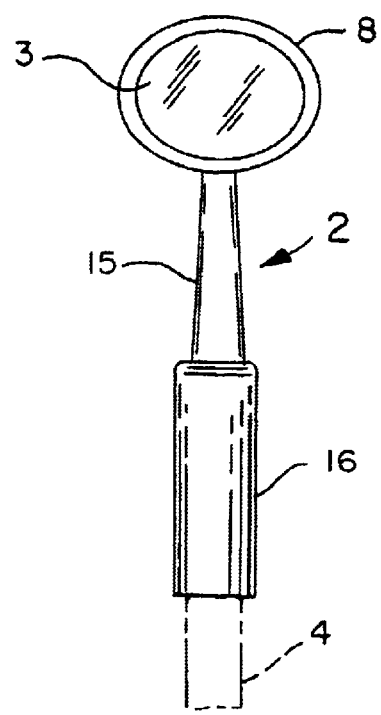
FIG. 2 is a Top plan view of a disposable mirror refill.
Figure 3:
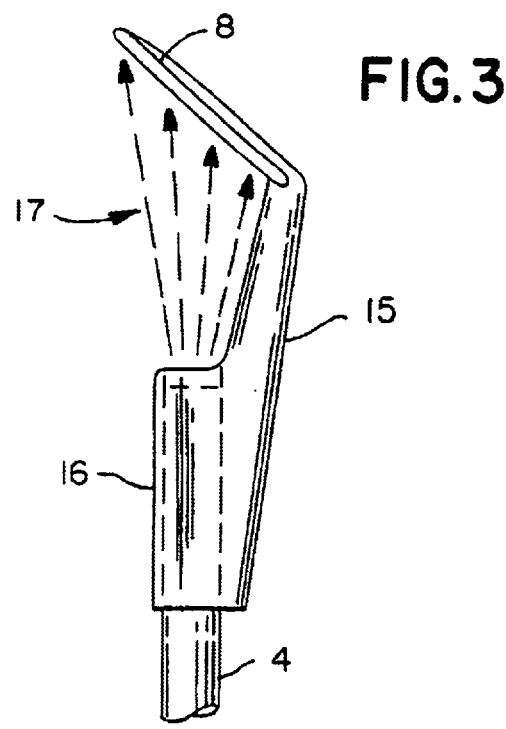
FIG. 3 is a Side elevational view of a disposable mirror refill showing a light path.

FIGS. 2 and 3 show disposable mirror refill 2. Hollow attachment collar 16 of mirror refill 2 slips over the distal end of elongated shank member 4. Support 15 attaches to angled mirror head 8 with reflecting surface 3. Light path 17 from a light source 21, such as a low heat light emitting diode lamp, shows illumination emanating from the hollow interior of collar 16.

FIG. 4 shows housing 20 with ridges 22 forming a fluted surface. This surface couples with the interior of attachment collar 16 of disposable mirror refill 2 in an interference fit while resisting rotation of mirror head 8.

FIG. 5 is a crossectional view of housing 20 showing the attachment to the reduced outer diameter of the distal end of elongated shank member 4.

The exploded view of FIG. 6 shows the power source 25, such as three cells in series, which fit within housing 5. Housing chamber 5 screws onto threads 26 of the forward portion. Although a single lithium cell or other type of battery can be used, the preferred embodiment uses three inexpensive alkaline cells such as the AG13/LR44 type which provide at least 15 hours of illumination. While housing chamber 5 is shown to be tubular, other geometric configurations such as cubes, spheres, egg shapes or rectangular boxes are possible.

FIG. 7 is a side crossectional view of an alternate embodiment 30 which uses a push button switch arrangement 37 as opposed to the rotary switch used in the preferred embodiment. Housing 35 encloses the power cells (not shown) and opens for service via mated threads 32. Switch element 31 is operated by push-button 34, which, when depressed, makes contact with power source (not shown) and wires 36 connected to light source 21, which push buttom 34 is held in place via elastomeric tube 33. Except for the different type of switch, this embodiment is similar to the preferred embodiment. A similar wiring arrangement with wires (not shown) connects the power source 25 utilized with rotary switch 6 to light source 21 in FIGS. 1 and 6.

Therefore, an ergonomic non-obstructive illuminated dental mirror 1 is provided without the need of fiber optics.

The mirror 1 includes the slim line elongated member 4, such as a tubular shank, having an electrical wire passage therein. The first end of elongated slim line member 4 engages hollow battery chamber 5. Low heat light source 21 is provided at the distal end of the slim line elongated member 4 at a second end thereof. Power source 25 rests in the battery chamber 5, which has an end cap secured to the first end on the slim line elongated member 4.

The removable disposable non-fogging angled reflective mirror head refill 2 is coupled to the second end of slim line elongated member 4. Light to the mirror is provided by low heat emitting light source 21, which is attached to the second end of the elongated member 4. The emitted light is directed toward the angled reflective mirror head refill 2. The power source 25 of FIG. 6 is connected to the low heat light source 21 by one or more conductive wires, such as wires 36 as shown in FIG. 7, within the wire passage connecting rotary switch 6 to light source 21 in FIG. 6, thereby forming a circuit 37 with the power source 25 and the light source 21, which is activated by the switch 31 connected to the conductive wire connection 36.

By virtue of its slim line ergonomic configuration, dental mirror 1 is easy to hold and easy to use.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

I claim:

1. An ergonomic non-obstructive illuminated examination mirror without the need of fiber optics comprising:

a slim line elongated member further including a wire passage, a weighted first end with a battery chamber and a grooved second end;

a power source resting in the battery chamber;

an end cap secured to the first end on said elongated member;

a removable disposable non-fogging angled reflective mirror head coupled to said grooved second end of said elonqated member in an interference fit;

a low heat emitting light source attached to the second end of said elongated member, said liqht source directed toward said angled reflective head;

at least one conductive wire within said wire passage and said end cap, said conductive wire forming a circuit with said power source and said light source; and, a switch connected to said conductive wire.

2. The ergonomic non-obstructive illuminated examination mirror of claim 1, wherein said angled reflective head is adjustable.

3. The ergonomic non-obstructive illuminated examination mirror of claim 1, wherein said second end of said slim line elongated member contains a grooved non-slip exterior surface.

4. The ergonomic non-obstructive illuminated examination mirror of claim 1, wherein said reflective head is chemically treated.

5. The ergonomic non-obstructive illuminated examination mirror of claim 1, wherein said switch is a rotary switch.

6. The ergonomic non-obstructive illuminated examination mirror of claim 1, wherein said switch is a push button switch.

7. The ergonomic non-obstructive illuminated examination mirror of claim 1, wherein said examination mirror is a dental examination mirror.

8. The ergonomic non-obstructive illuminated examination mirror of claim 1, wherein said examination mirror is a medical examination mirror.

9. The ergonomic non-obstructive illuminated examination mirror of claim 1, wherein said examination mirror is a surgical examination mirror.

10. An ergonomic non-obstructive illuminated examination mirror without the need of fiber optics comprising:

a slim line elongated member further including a wire passage, a weighted first end with a battery chamber and a second end;

a power source resting in the battery chamber; an end cap secured to the first end on said elongated member;

a removable disposable non-fogging angled reflective mirror head coupled to the second end of said elongated member in an interference fit;

a low heat emitting light source attached to the second end of said elongated member, said light source directed toward said angled reflective head;

at least one conductive wire within said wire passage and said end cap, said conductive wire forming a circuit with said power source and said light source;

a switch connected to said conductive wire, wherein said first end of the slim line elongated member contains a non-slip exterior surface; and, wherein said grooved non-slip exterior surface comprises a plurality of with ridges forming a fluted surface coupling with an interior of an attachment collar of said removable disposable non-fogging angled reflective mirror head in an interference fit.

11. The ergonomic non-obstructive illuminated examination mirror of claim 10, wherein said angled reflective head is adjustable.

12. The ergonomic non-obstructive illuminated examination mirror of claim 10, wherein said reflective head is chemically treated.

13. The ergonomic non-obstructive illuminated examination mirror of claim 10, wherein said switch is a rotary switch.

14. The ergonomic non-obstructive illuminated examination mirror of claim 10, wherein said switch is a push button switch.

15. The ergonomic non-obstructive illuminated examination mirror of claim 10, wherein said examination mirror is a dental examination mirror.

16. The ergonomic non-obstructive illuminated examination mirror of claim 10, wherein said examination mirror is a medical examination mirror.

17. The ergonomic non-obstructive illuminated examination mirror of claim 10, wherein said examination mirror is a surgical examination mirror.

* * * * *